United States Patent
Denti

(12) 
(10) Patent No.: US 7,559,929 B2
(45) Date of Patent: Jul. 14, 2009

(54) IMPLANTS AND METHODS FOR POSITIONING SAME IN SURGICAL APPROACHES TO THE SPINE

(75) Inventor: Aldo Denti, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 298 days.

(21) Appl. No.: 11/061,400

(22) Filed: Feb. 18, 2005

(65) Prior Publication Data

US 2006/0200129 A1    Sep. 7, 2006

(51) Int. Cl.
*A61F 5/00* (2006.01)
*A61B 17/70* (2006.01)

(52) U.S. Cl. .................................. 606/86 A; 606/261
(58) Field of Classification Search ............ 606/61, 606/72–73, 103, 279, 280, 250, 265, 274, 606/261, 86 A, 262, 263, 264, 301, 305, 308, 606/309
See application file for complete search history.

(56) References Cited

U.S. PATENT DOCUMENTS

| | | | |
|---|---|---|---|
| 4,743,260 A * | 5/1988 | Burton | 128/898 |
| 4,790,297 A * | 12/1988 | Luque | 606/61 |
| 4,887,595 A | 12/1989 | Heinig et al. | |
| 4,898,186 A * | 2/1990 | Ikada et al. | 606/62 |
| 4,957,497 A | 9/1990 | Hoogland et al. | |
| 5,005,562 A * | 4/1991 | Cotrel | 606/61 |
| 5,152,303 A * | 10/1992 | Allen | 128/898 |
| 5,176,679 A | 1/1993 | Lin | |
| 5,261,911 A | 11/1993 | Carl | |
| 5,261,913 A * | 11/1993 | Marnay | 606/61 |
| 5,382,248 A * | 1/1995 | Jacobson et al. | 606/60 |
| 5,387,212 A | 2/1995 | Yuan et al. | |
| 5,403,316 A | 4/1995 | Ashman | |
| 5,527,315 A | 6/1996 | Jeanson et al. | |
| 6,235,028 B1 | 5/2001 | Brumfield et al. | |
| 6,443,953 B1 * | 9/2002 | Perra et al. | 606/61 |
| 6,540,748 B2 * | 4/2003 | Lombardo | 606/264 |
| 6,682,530 B2 | 1/2004 | Dixon et al. | |
| 7,018,379 B2 * | 3/2006 | Drewry et al. | 606/279 |
| 2002/0026194 A1 | 2/2002 | Morrison et al. | |
| 2003/0220643 A1 | 11/2003 | Ferree | |
| 2004/0049189 A1 * | 3/2004 | Le Couedic et al. | 606/61 |

FOREIGN PATENT DOCUMENTS

FR    2 692 775 A1    6/1992
FR    2 711 909 A1    11/1993

* cited by examiner

*Primary Examiner*—Pedro Philogene

(57) ABSTRACT

Implants and methods for positioning the implant facilitate placement and guiding of the implant to an implantation location adjacent the spinal column. The implant includes a spinal rod having at least one passage therethrough for receiving a guiding member extending from the surgical location. The implant is moveable along the guiding member to the surgical location for securement with a bone anchor engaged to the patient.

35 Claims, 5 Drawing Sheets

IMPLANTS AND METHODS FOR POSITIONING SAME IN SURGICAL APPROACHES TO THE SPINE

BACKGROUND

Techniques and systems have been developed for stabilizing and correcting deformities in the spinal column. Some techniques include positioning an implant along the spinal column and engaging the implant to the spinal column with bone fasteners. Other techniques require the assembly of components of either the fasteners or the stabilization construct adjacent the spinal column.

It is desirable to minimize the intrusion into the muscle, tissue, nerves and other anatomical structures during spinal surgery. Minimally invasive techniques reduce trauma, facilitate healing, and reduce post-operative recovery time for the patient. However, the room available in the approach to the surgical site may hinder placement of the implant along the spinal column.

Accordingly, there remains a need for systems and methods to facilitate minimally invasive surgical techniques for positioning implants adjacent the spinal column. Such systems and techniques may also have application in open surgical techniques. The present invention is directed to meeting these needs, among others.

SUMMARY

According to one aspect, a system for spinal stabilization includes a bone anchor, a guide member and a spinal rod. The bone anchor includes a bone engagement portion and a lumen extending axially therealong. The guide member is engageable to the vertebra and includes an elongated body sized for receiving the lumen of the anchor. The anchor is movable along the guide member for engagement with the vertebra. The spinal rod includes an elongated body extending along a longitudinal axis. The body includes a passage extending trans-axially therethrough. The spinal rod is positionable about the guide member with the guide member received in the passage. The spinal rod is movable along the guide member toward the anchor when the guide member and the anchor are engaged to the vertebra.

According to another aspect, a minimally invasive surgical system includes a spinal rod, at least two bone anchors, and at least two guide members. The spinal rod is positionable within a body of a patient and includes at least one trans-axial passage therethrough. The bone anchors each include a distal bone engaging portion and a proximal head portion. Each of the bone anchors further includes a lumen extending axially therethrough. The guide members are engageable to a bony structure within the patient and are sized to allow passage of a respective one of the bone anchors thereover to guide engagement of the bone anchors to the bony structure. Each of the guide members are receivable in the at least one passage of the spinal rod to guide the spinal rod into engagement with the at least two bone anchors.

According to a further aspect, a minimally invasive surgical method comprises: engaging a distal end of a guide member to at least one vertebra in a patient, wherein the guide member is elongated and extends proximally from the bony tissue to a location outside the patient; advancing a bone anchor along the guide member to the at least one vertebra; engaging the bone anchor to the at least one vertebra; positioning a spinal rod about the guide member; advancing the spinal rod along the guide member to the bone anchor; and securing the spinal rod to the bone anchor.

According to another aspect, a minimally invasive surgical method comprises: engaging distal ends of first and second elongated guide members to at least one vertebra in a patient in a minimally invasive surgical approach to the at least one vertebra; guiding first and second bone anchors along respective ones of the first and second bone anchors to the at least one vertebra through the minimally invasive surgical approach; engaging the first and second bone anchors to the at least one vertebra; positioning a spinal rod about each of the first and second guide members; guiding the spinal rod along the first and second guide members to the bone anchors; and securing the spinal rod to the first and second bone anchors.

These and other aspects are also discussed below.

DESCRIPTION OF THE ILLUSTRATED EMBODIMENTS

Figure 1:
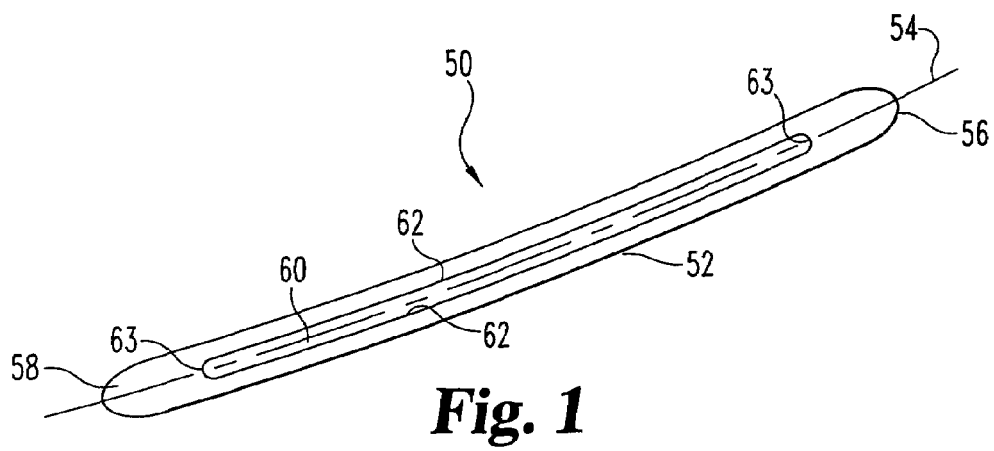
FIG. 1 is an elevation view of one embodiment implant.

For the purposes of promoting an understanding of the principles of the invention, reference will now be made to embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

An implant is positionable along the spinal column and receivable in a receiver of an anchor engaged to one or more vertebrae of the spinal column. A guide member extends from the anchor, and is received by the implant as the implant is advanced toward the receiver of the anchor. The guide member can also be employed to guide placement and engagement of the anchor to one or more vertebrae. In one embodiment, the implant is an elongated spinal rod having at least one trans-axial passage therethrough for receiving the guide member.

In FIG. 1 there is shown one embodiment of an implant 50 in the form of a spinal rod having an elongated body 52 extending along longitudinal axis 54. Body 52 includes a first end 56 and an opposite second end 58, and a length therebetween. Ends 56, 58 can be tapered, rounded, square or otherwise include any suitable configuration for implantation in a body of a patient. Body 52 further includes a passage 60 extending transversely to longitudinal axis 54 and opening along opposite sides of body 52. Passage 60 is oriented to extend trans-axially and receives one or more guide members to guide placement of implant 50 adjacent to one or more vertebrae of the patient.

Implant 50 is positionable along one or more vertebrae and engageable thereto with anchors engaged to the one or more vertebrae. The implant includes an elongated body, and in one embodiment is in the form of a spinal rod having a circular cross-section transverse to longitudinal axis 54. Non-circular cross-sections along all or a portion of the length of implant 50 are also contemplated. The cross-section can be uniform or variable along the length of implant 50. Implant 50 can be solid, hollow, porous, non-porous, fenestrated, pitted, knurled, threaded, grooved, spiked, or any combination thereof. The implant can be engaged to bony structure such as adjacent vertebrae of the spinal column, or any other adjacent bony portions separated by a joint, fracture, defect, or condition, for example.

In FIG. 1 body 52 has a linear configuration. Other embodiments contemplate other configurations for body 52. For example, body 52 can be curved about a radius along longitudinal axis 54. Still other embodiments contemplate that body 52 includes a compound curvature, multiple linear segments with longitudinal axes transversely oriented relative to one another, or a combination of one or more linear segments and one or more curved segments. In still a further form, body 52 can include one or more hinges or flexible joints. It is further contemplated that body 52 can be bendable, and elastic so as to return toward its pre-bent state, or inelastic so that the bent state is maintained. It is still further contemplated that body 52 can be made from a shape memory material, including shape memory metals, polymers and composites. Body 52 can also be made from any bio-compatible material, including metal and metal alloys, polymers, ceramics, resorbable material and non-resorbable material, and synthetic and non-synthetic materials, for example.

Figure 2:
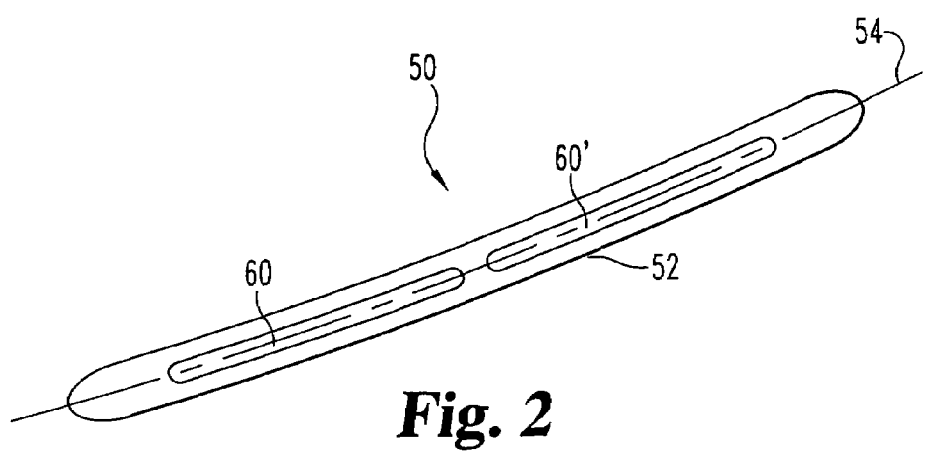
FIG. 2 is an elevation view of another embodiment implant.
Figure 3:
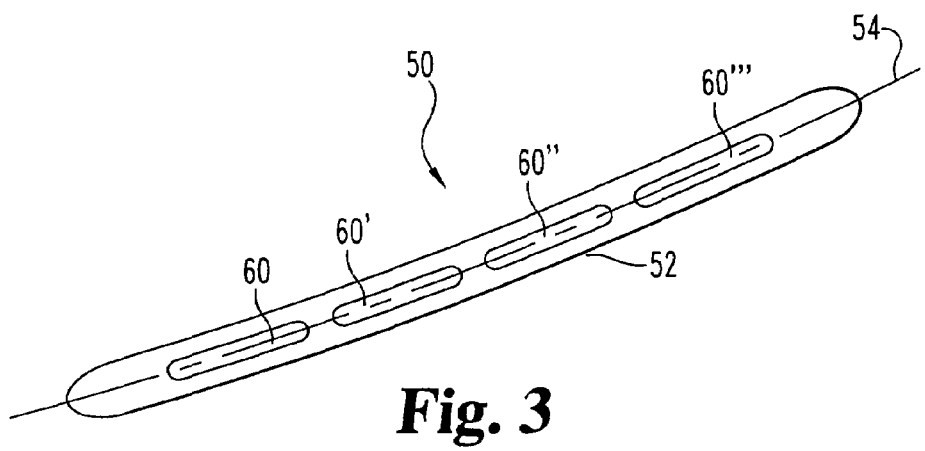
FIG. 3 is an elevation view of another embodiment implant.

In FIG. 1 body 52 defines passage 60 extending trans-axially along substantially the entire length of body 52 to locations adjacent ends 56, 58. Other embodiments contemplate that body 52 is provided with two trans-axial passages 60, 60', as shown in FIG. 2. In still other embodiments, more than two passages 60 are contemplated, as shown in FIG. 3, which shows four trans-axial passages 60, 60', 60", and 60'". The passages are spaced along longitudinal axis 54 and can be elongated to facilitate alignment of body 52 with the guide member, as discussed further below. In the illustrated embodiment, passage 60 includes linear sides 62 and rounded ends 63, forming an oval or racetrack shaped configuration along longitudinal axis 54. Other embodiments contemplate other shapes, including circular, polygonal, and other non-circular shapes.

Figure 4:
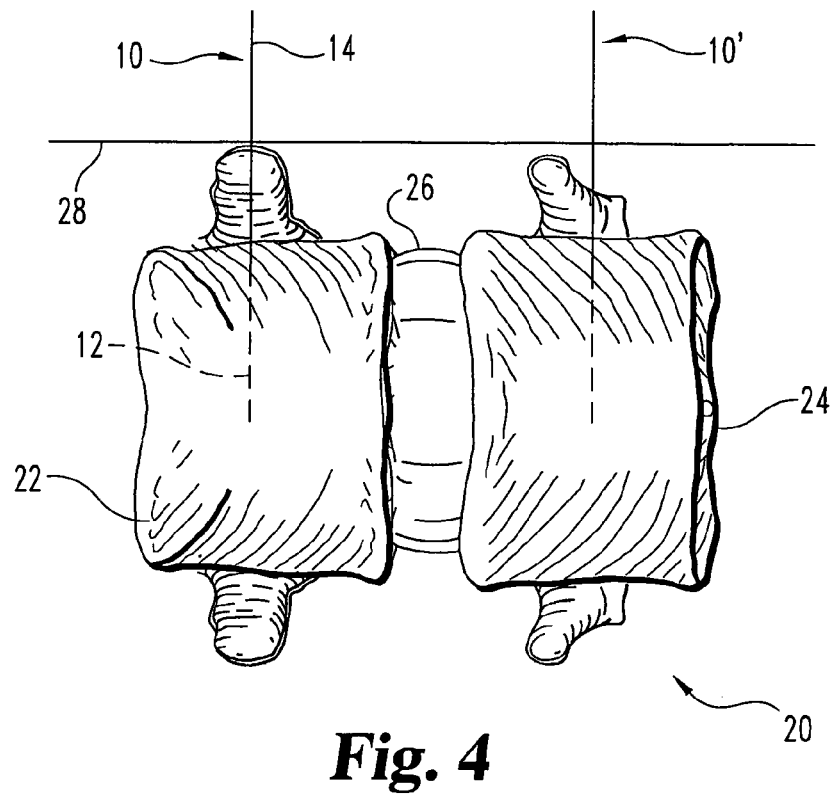
FIG. 4 is a diagrammatic view of spinal column segment with guide members engaged to vertebrae.

Referring to FIG. 4, there is shown diagrammatically a spinal column segment 20 including a first vertebra 22, a second vertebra 24, and a disc space 26 therebetween. It should be understood, however, that the procedure discussed herein has application with stabilization of one vertebra or three or more vertebrae. In addition, such stabilization can be performed at any region of the spinal column, including the cervical, thoracic, lumbar and sacral regions, and in any approach or combination of approaches to the spinal column, including anterior, antero-lateral, lateral, posterior, postero-lateral approaches, for example. The guide members, anchors and implants can be engaged to any portion of the vertebrae, including the anterior portion of the vertebral body or any of the posterior elements of the vertebral body.

In FIG. 4 a first guide member 10 includes a distal end 12 engaged to bony tissue of vertebra 22 and extends proximally therefrom through tissue 28 to a location adjacent or proximal of the skin level of the patient. Guide member 10 can extend through tissue 28 to facilitate access to proximal end 14 thereof. Other embodiments contemplate guide member 10 is positioned at or recessed below the skin level. A second guide member 10' is similarly engaged to and extends proximally from vertebra 24. In one embodiment, guide members 10, 10' are guidewires employed in surgical procedures to guide placement of cannulated dilators, anchors, instruments and implants along a desired surgical path through a minimally invasive approach.

Guide member 10 can be positioned by a surgical guidance or imaging system to ensure engagement of distal end 12 at the desired location relative to the respective vertebra. In one procedure, a cannulated needle is provided with a removable stylet in the needle cannula. The needle and stylet are positioned through tissue 28 for engagement with the vertebra at the desired location. The stylet is then removed, and guide member 10 is positioned through the cannulated needle to engage the vertebra. The needle is then removed and subsequent procedures are completed using the guide member 10. In other procedures guide member 10 is guided with imaging techniques or via freehand through percutaneous, minimally invasive approaches or open, retracted incisions.

Figure 5:
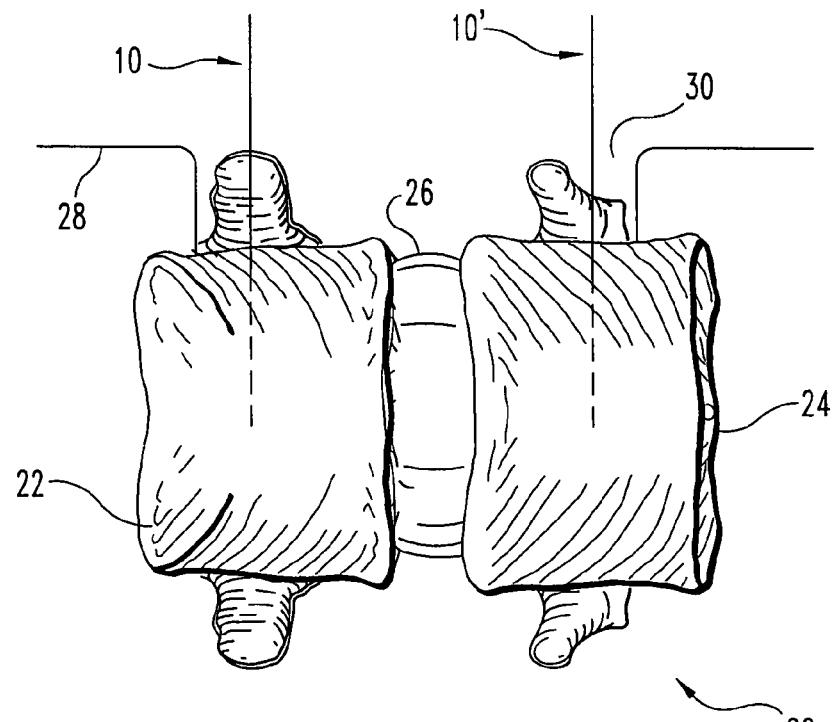
FIG. 5 is a diagrammatic view of the spinal column segment with tissue retracted according to one procedure.
Figure 6:
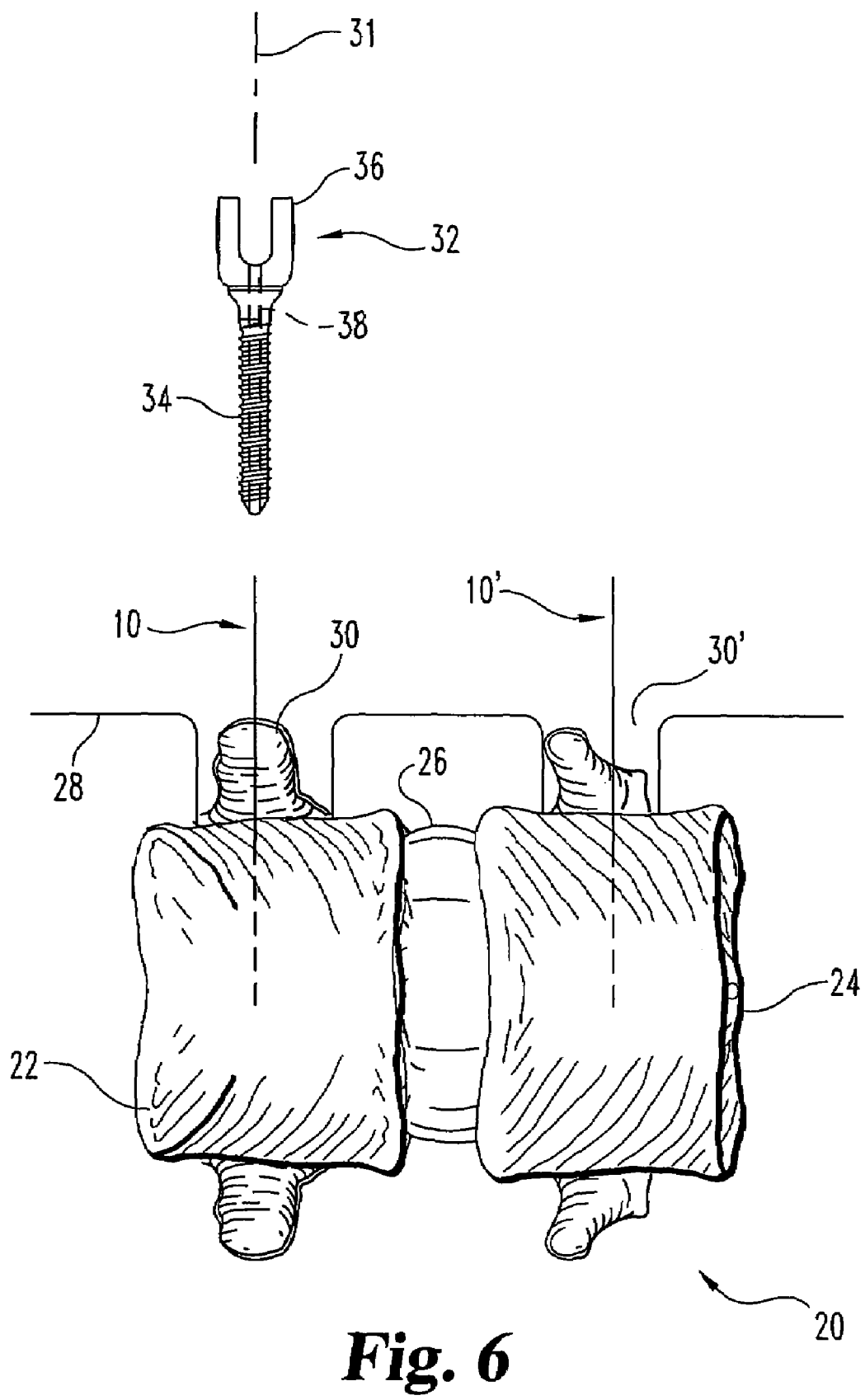
FIG. 6 is a diagrammatic view of the spinal column segment with tissue retracted according to another procedure and an anchor being positioned toward a guide member.

In FIG. 5, a retracted access portal 30 in tissue 28 is shown that extends between guide members 10, 10'. In this embodiment, an incision can be made between adjacent guide members, and one or more retractors, sleeves, or other devices can be placed in the incision to maintain tissue our of the surgical path to the vertebrae. Anchors, implants and other devices and procedures can be placed or performed adjacent the vertebrae through the retracted tissue path. In FIG. 6, there is shown an access portal 30 associated with guide member 10, and a second access portal 30' associated with guide member 10'. In this embodiment, one or more dilators can be positioned over the respective guide members to provide a dilated tissue path about the guide member to the vertebra. In still another example, the guide member can be employed to percutaneously guide an anchor to the vertebra through a micro-incision without any tissue dilation or retraction. Anchors, implants and other devices and procedures can be placed or performed adjacent the vertebra through the dilated tissue or micro-incision.

Any of the approaches to the vertebra discussed herein can be employed in the procedure. Accordingly, in FIGS. 7-10, the tissue 28 and access portal(s) to the one or more vertebrae are not shown, it being understood that any suitable approach or approaches are contemplated. In FIG. 6 there is shown an anchor 32 prior to placement about guide member 10. Anchor 32 may include a distal bone engaging portion 34 and a proximal receiver 36 for receiving implant 50. A lumen 38 extends axially through bone engaging portion 34 along a longitudinal axis 31 and opens into receiver 36.

Figure 9:
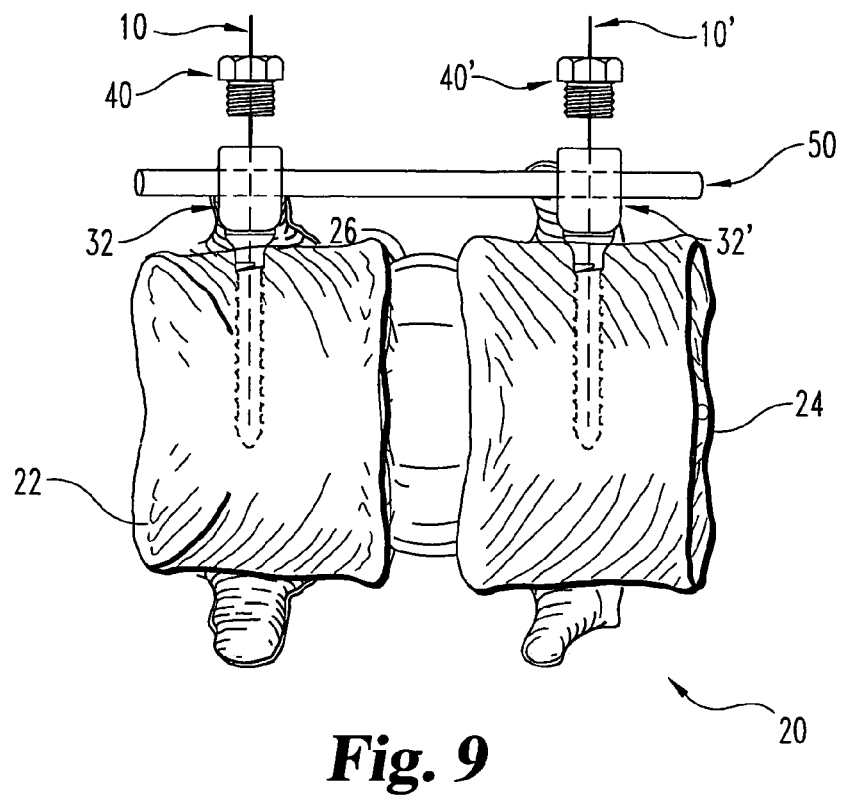
FIG. 9 is a diagrammatic view of the spinal column segment of FIG. 8 with engaging members being guided toward the implant seated in the anchors.
Figure 10:
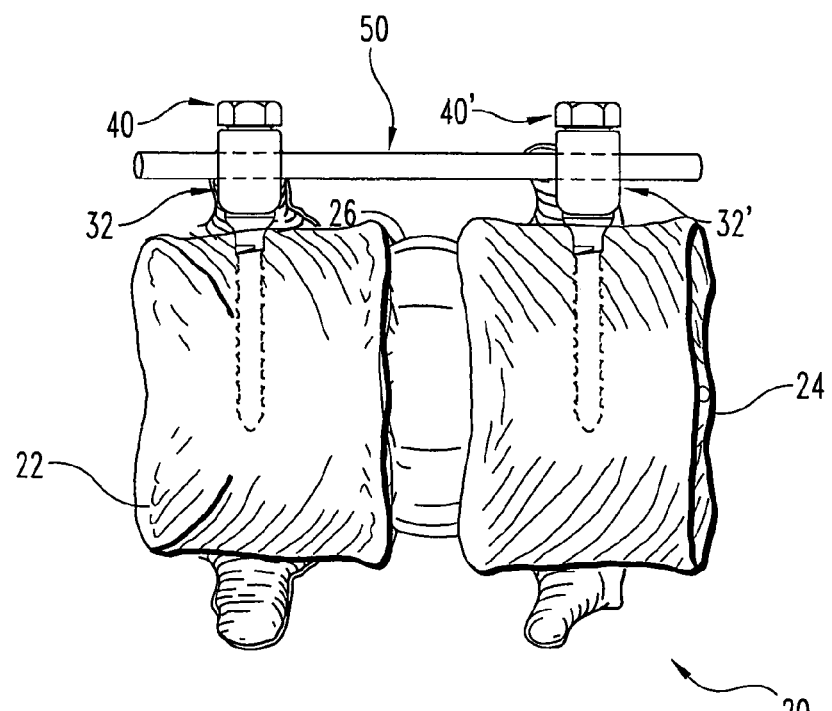
FIG. 10 is a diagrammatic view of the spinal column segment of FIG. 9 with engaging members engaged to the anchors and the guide members removed.

In one embodiment, anchor 32 is a bone screw with a threaded shaft comprising bone engaging portion 34 and a U-shaped head comprising receiver 36. Receiver 36 includes a pair of arms extending about opposite sides of a receptacle sized and shaped to receive implant 50 in direction extending transversely to axis 31 between the arms of receiver 36. In one embodiment, the arms include internal threads to threadingly engage an externally threaded set screw, such as is illustrated for engaging member 40 (FIGS. 9, 10.) Other embodiments contemplate other configurations for receiver 36 that secure implant 50 in, on or about receiver 36 alone or in combination with an engaging member such as a set screw, plug, clamp, nut washer, crown, or cap, for example.

Receiver 36 can be pivotally coupled to bone engaging portion 34 to provide a multi-axial anchor assembly. In another embodiment, receiver 36 is fixed relative to bone engaging portion 34 to provide a uni-axial arrangement. Receiver 36 can be offset to one side or the other relative to bone engaging portion 34, or aligned axially as shown. Bone engaging portion 34 can be a threaded shaft configured for insertion in a hole that is drilled and tapped in the bony tissue, or may be provided with a self-drilling and/or self-tapping thread configuration. Other embodiments contemplate other forms for bone engaging portion 34, including a hook shape, staple, inter-body implant, or shaft with barbs, gulls, teeth or other bone engaging form.

Figure 7:
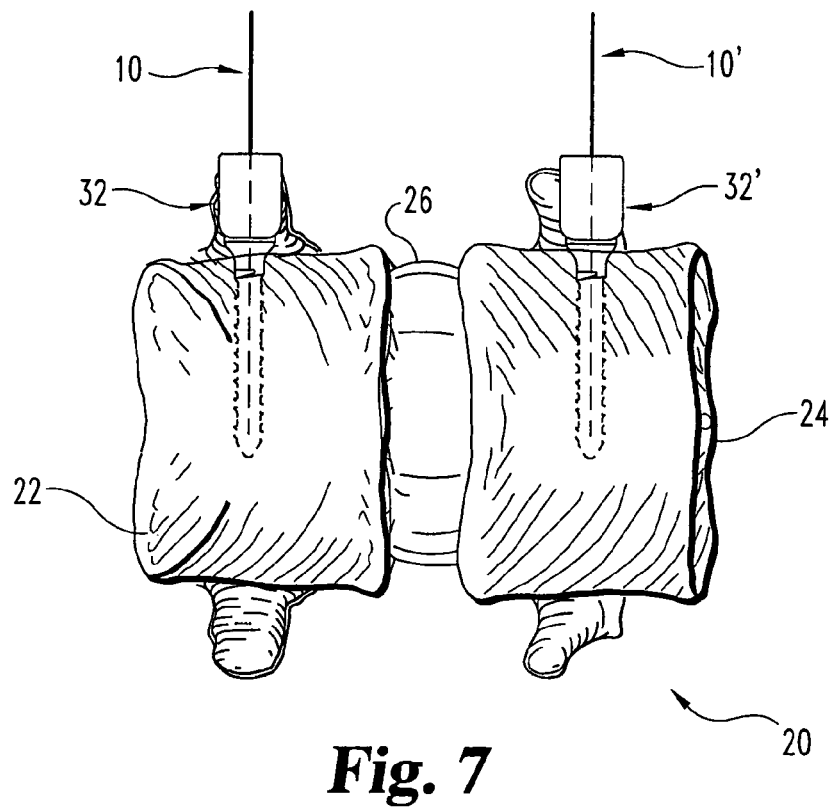
FIG. 7 is a diagrammatic view of the spinal column segment of FIG. 4 with anchors engaged to the vertebrae.

As shown in FIG. 7, each of the anchors 32, 32' have been guided along the respective guide member 10, 10' and engaged to the respective vertebra 22, 24. Prior to engagement of anchors 32, 32', drilling or tapping of the holes to receive the bone engaging portion could be completed with cannulated drills, awls and taps, as necessary, guided by the respective guide members 10, 10'. In addition, procedures and implants could be performed or positioned in disc space 26 through the same approach or through a different approach as that provided by guide members 10, 10'. After engagement of anchors 32, 32' to the respective vertebrae 22, 24, guide members 10, 10' can remain engaged to vertebrae 22, 24 and extend proximally from anchors 32, 32'.

Figure 8:
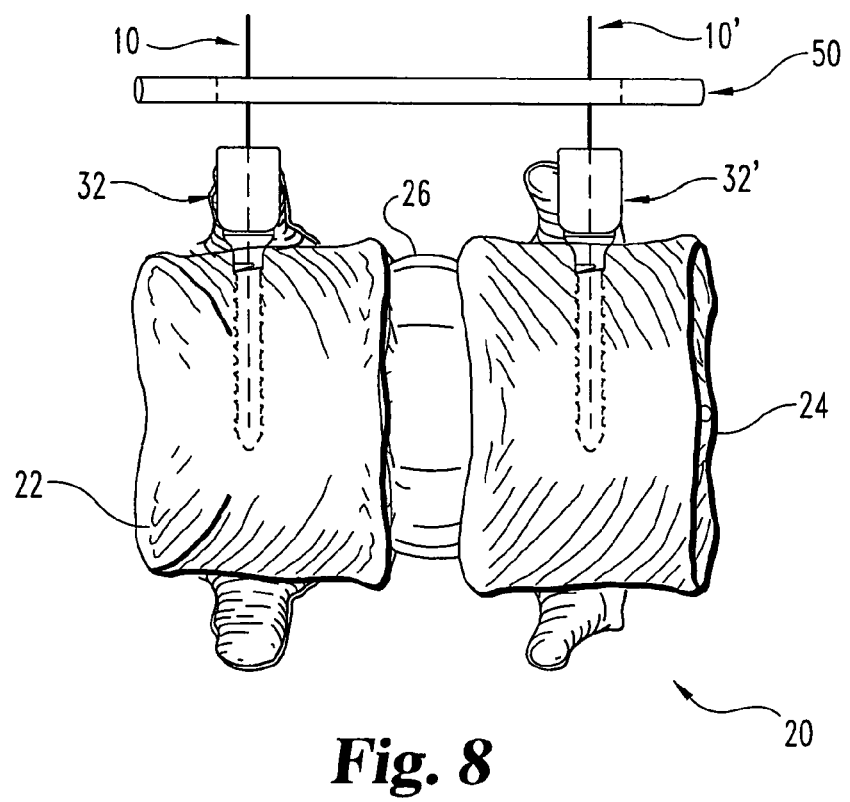
FIG. 8 is a diagrammatic view of the spinal column segment of FIG. 7 with an implant being guided to the anchors with a guide member.

In FIG. 8 implant 50 is positioned so that the proximal ends of guide members 10, 10' are received through passage or passages 60 of implant 50. As shown in FIG. 9, implant 50 is guided along guide members 10, 10' and seated in receivers 36 of anchors 32, 32'. Engaging members 40, 40' can each include a central lumen that receives the respective guide member 10, 10' and allows the respective engaging member 40, 40' to be guided therealong for engagement with the respective anchor 32, 32', as shown in FIG. 10. Engaging members 40, 40' maintain and secure implant 50 to anchors 32, 32', and may include any suitable form as discussed above. After securement of implant 50, guide members 10, 10' may be disengaged from vertebrae 22, 24 and removed from the patient.

Guide members 10 can be bendable to facilitate placement of implant 50 adjacent anchors 32, 32' in minimally invasive surgical approaches and other approaches where bending and maneuvering of guide member 10 may be useful to avoid anatomical structures or surgical instruments. In addition, the procedure contemplates that more than two guide members and anchors may be employed in, for example, multi-level stabilization procedures of the spinal column. In one embodiment, a guide member is provided with each anchor to guide the implant to the anchors. In another embodiment, a guide member is employed with less than all the anchors engaged to vertebrae in the procedure. Other procedures contemplate placement of multiple implants along one or more vertebral levels and along the same vertebral level or levels in bi-lateral approaches.

It is also contemplated that guiding members 10, 10' can be positioned to facilitate tissue retraction or move other anatomical structures positioned therealong during the surgical procedure. In still other techniques, compression or distraction forces can be applied to anchors 32, 32' prior to securement of implant 50 to both of the anchors. The positioning of instruments to employ such forces can be facilitated with guide members 10, 10'. Such forces can be applied to provide compression on an implant or other device in disc space 26, to correct curvature of the spinal column segment to which implant 50 is to be attached, and/or to increase or decrease the spacing between vertebrae 22, 24.

While embodiments of the invention have been illustrated and described in detail in the drawings and foregoing description, the same is to be considered as illustrative and not restrictive in character, it being understood that all changes and modifications that come within the spirit of the invention are desired to be protected.

What is claimed is:

1. A system for spinal stabilization, comprising:
   a bone anchor engageable to a vertebra, said bone anchor including a bone engagement portion and a receiver at a proximal end of said bone engagement portion, said receiver including a pair of arms extending along opposite sides of a receptacle of said receiver, said receptacle extending and opening transversely to said pair of arms and at a proximal end of said pair of arms, said bone anchor further including a lumen extending axially there along that opens into said receptacle between said pair of arms;
   a guide member engageable to the vertebra, said guide member including an elongated body positioned in said lumen of said anchor with said guide member extending through said receptacle and proximally of said pair of arms, said body of said guide member being sized for receiving said lumen of said anchor so that said anchor is movable along said guide member for engagement with the vertebra with said guide member extending from said lumen into said receptacle;
   a spinal rod including an elongated, cylindrical body extending along a longitudinal axis, said body including a passage extending trans-axially therethrough, said spinal rod being positioned about said guide member with said guide member received in said passage while said spinal rod is positioned in said receptacle of said receiver and between said pair of arms, said spinal rod being movable along said guide member toward said anchor when said guide member and said anchor are engaged to the vertebra, wherein when said spinal rod is positioned in said receptacle of said receiver said guide member extends through said passage of said spinal rod and proximally of said spinal rod and said pair of arms; and
   an engaging member defining a central lumen for receiving said guide member, said engaging member positioned between said pair of arms and engaged to said anchor member for securing said spinal rod in said receiver between said pair of arms, wherein said guide member simultaneously extends through said lumen of said anchor, said passage of said spinal rod, and said lumen of said engaging member and extends proximally from said engaging member so that said guide member is removable from lumens of said anchor and said engaging member and said passage of said spinal rod.

2. The system of claim 1, wherein said bone anchor is a bone screw.

3. The system of claim 2, wherein said bone engaging portion is a threaded shaft.

4. The system of claim 3, wherein said receiver portion is a U-shaped saddle.

5. The system of claim 4, wherein said spinal rod is bendable and elastic to return toward a pre-bent shape.

6. The system of claim 1, wherein said guide member is a guidewire.

7. The system of claim 1, wherein said spinal rod includes tapered ends.

8. The system of claim 7, wherein said body includes a circular cross-section transverse to said longitudinal axis.

9. The system of claim 1, wherein said passage is elongated and extends substantially along an entire length of said body of said spinal rod.

10. The system of claim 1, wherein said passage includes at least two passages spaced along said longitudinal axis of said body.

11. The system of claim 1, wherein said passage includes a racetrack shape with elongated sides extending along said longitudinal axis.

12. A minimally invasive surgical system, comprising:
an elongated, cylindrical spinal rod positionable within a body of a patient, said spinal rod extending along a longitudinal axis including at least one trans-axial passage therethrough;
at least two bone anchors each including a distal bone engaging portion and a proximal head portion, said proximal head portions each including a pair of arms that define a receptacle therebetween, said receptacle extending and opening transversely to said pair of arms and opening at a proximal end of said pair of arms, each of said bone anchors including a lumen extending axially therethrough and said lumen opens into said receptacle of said bone anchor; and
at least two guide members engageable to a bony structure within the patient and positioned in said lumen of a respective one of said bone anchors with said guide members extending from said lumen and through said receptacle of said respective bone anchor, said guide members each being configured to guide engagement of said bone anchor to the bony structure, each of said guide members further being positioned through said at least one passage of said spinal rod with said spinal rod positioned in said receptacles of said at least two bone anchors, said guide members and said passages being arranged to guide said spinal rod toward said at least two bone anchors for engagement therewith in said receptacles of said bone anchors when said bone anchors are engaged to the bony structure; and
at least two engaging members each defining a central lumen for receiving respective ones of said at least two guide members, said at least two engaging members each being positioned between said pair of arms and engaged in said receptacle of a respective one of said at least two bone anchors for securing said spinal rod in said receptacle thereof with said at least two guide members extending proximally from said respective engaging member, wherein when said engaging members secure said spinal rod to said bone anchors each of said at least two guide members simultaneously extends through said lumen of said respective anchor, said at least one passage of said spinal rod, and said lumen of said respective engaging member so that guide member is removable from said lumens of said anchor and said engaging member and said at least one passage of said spinal rod.

13. The system of claim 12, wherein each of said bone anchors includes a head portion that is pivotally coupled to said bone engaging portion and movable relative to said bone engaging portion to form a multi-axial anchor assembly.

14. The system of claim 13, wherein said bone engaging portion is a threaded shaft.

15. The system of claim 14, wherein said receiver portion is a U-shaped saddle.

16. The system of claim 12, wherein said spinal rod is bendable and elastic to return toward a pre-bent shape.

17. The system of claim 12, wherein said engaging member each includes an externally threaded set screw portion that threadingly engage internal threads along said pair of arms to secure said spinal rod in said receptacle.

18. The system of claim 12, wherein said guide member is a guidewire.

19. The system of claim 12, wherein said spinal rod includes a body having a circular cross-section transverse to said longitudinal axis said circular cross-section extending between opposite ends of said spinal rod and said opposite ends are tapered.

20. The system of claim 12, wherein said at least one passage is elongated and extends along a substantial portion of a length of said spinal rod.

21. The system of claim 12, wherein said at least one passage includes at least two passages spaced along said longitudinal axis of said spinal rod.

22. A minimally invasive surgical method, comprising:
engaging a distal end of a guide member to at least one vertebra in a patient, wherein the guide member is elongated and extends proximally from the at least one vertebra to a location outside the patient;
advancing a bone anchor along said guide member to the at least one vertebra, wherein the bone anchor includes a receptacle that opens proximally;
engaging the bone anchor to the at least one vertebra so that the guide member extends proximally from a lumen of the bone anchor that opens into the receptacle;
positioning a spinal rod about the guide member after engaging the bone anchor to the at least one vertebra;
advancing the spinal rod along the guide member to guide the spinal rod into the receptacle of the bone anchor;
positioning an engaging member about the guide member after advancing the spinal rod into the receptacle of the bone anchor;
advancing the engaging member along the guide member and into the receptacle of the bone anchor;
securing the spinal rod in the receptacle of the bone anchor with the engaging member engaged to the bone anchor; and
withdrawing the guide member proximally through the bone anchor, the spinal rod and the engaging member.

23. The method of claim 22, further comprising:
engaging a distal end of a second guide member to a second vertebra in a patient, wherein the second guide member is elongated and extends proximally from the second vertebra to a location outside the patient;
advancing a second bone anchor along said second guide member to the second vertebra;
engaging the second bone anchor to the second vertebra;
positioning the spinal rod about the second guide member;
simultaneously advancing the spinal rod along each of the guide members to each of the bone anchors; and
securing the spinal rod in receptacles of each of the bone anchors.

24. The method of claim 23, further comprising moving engaging members along each of the guide members and engaging the engaging members within the to receptacle of respective ones of the bone anchors to secure the spinal rod in each of the bone anchors.

25. The method of claim 23, wherein the spinal rod includes one passage extending transversely to a central longitudinal axis thereof and positioning the spinal rod includes positioning each of the guide members in the passage.

26. The method of claim 23, wherein the spinal rod include first and second passages spaced therealong extending transversely to a central longitudinal axis of the spinal rod and positioning the spinal rod includes positioning the guide members in respective ones of the passages.

27. The method of claim 23, wherein each of the guide members is a guidewire.

28. The method of claim 22, wherein the spinal rod includes a passage extending transversely to a central longitudinal axis of the spinal rod and the guide member is received in the passage, the spinal rod further includes a circular cross-section along its length that extends between opposite ends that are tapered.

29. A minimally invasive surgical method, comprising:
engaging distal ends of first and second elongated guide members to at least one vertebra in a patient in a minimally invasive surgical approach to the vertebra;
guiding first and second bone anchors along respective ones of the first and second guide members to the at least one vertebra through the minimally invasive surgical approach, the first and second bone anchors each including a receiver portion with a receptacle at a proximal end thereof and a lumen opening into said receptacle thereof that extends from said opening to a distal end of said respective bone anchor;
engaging the first and second bone anchors to the at least one vertebra with the first and second guide members extending through receptacles of respective ones of the first and second bone anchors;
positioning an elongated, cylindrical spinal rod about each of the first and second guide members after engaging the first and second bone anchors to the at least one vertebra;
guiding the spinal rod along the first and second guide members and into the receptacles of each of the bone anchors;
guiding first and second engaging members along respective ones of the first and second guide members and into the receptacles of the first and second bone anchors after guiding the spinal rod into the receptacles of each of the bone anchors;
securing the spinal rod to the first and second bone anchors with the first and second engaging members engaged to the first and second bone anchors; and
removing the first and second guide members from the first and second bone anchors, the spinal rod and the first and second engaging members after securing the spinal rod to the first and second bone anchors.

30. The method of claim 29, further comprising removing the first and second guide members from the patient.

31. The method of claim 29, further comprising threadingly engaging the first and second engaging members to internal threads along the receiver portion of the first and second bone anchors.

32. The method of claim 29, wherein securing the spinal rod includes seating the spinal rod in U-shaped receptacles of the receiver portion of the first and second bone anchors.

33. The method of claim 29, wherein the spinal rod includes one passage extending transversely to a central longitudinal axis thereof and positioning the spinal rod includes positioning each of the guide members in the passage of the spinal rod.

34. The method of claim 29, wherein the spinal rod includes first and second passages spaced therealong extending transversely to a central longitudinal axis thereof and positioning the spinal rod includes positioning the guide members in respective ones of the passages of the spinal rod.

35. The method of claim 29, wherein each of the guide members is a guidewire and the spinal rod includes a cross-section that forms a circle along a length of spinal rod between opposite ends of the spinal rod.

* * * * *